(12) United States Patent
Umeda et al.

(10) Patent No.: US 8,541,468 B2
(45) Date of Patent: Sep. 24, 2013

(54) OPHTHALMIC COMPOSITION FOR TREATING TEAR DYSFUNCTION

(75) Inventors: Yuzuru Umeda, Toyama (JP); Hideo Nakashima, Toyooka (JP); Michiko Shibuya, Toyooka (JP); Yasukazu Saitoh, Shobara (JP); Shoji Okada, Toyooka (JP); Shigeru Nakamura, Toyooka (JP)

(73) Assignee: Ophtecs Corporation, Osaka-shi (JP)

( * ) Notice: Subject to any disclaimer, the term of this patent is extended or adjusted under 35 U.S.C. 154(b) by 694 days.

(21) Appl. No.: 10/574,615

(22) PCT Filed: Sep. 30, 2004

(86) PCT No.: PCT/JP2004/014774
§ 371 (c)(1),
(2), (4) Date: Apr. 20, 2007

(87) PCT Pub. No.: WO2005/032534
PCT Pub. Date: Apr. 14, 2005

(65) Prior Publication Data
US 2007/0225369 A1    Sep. 27, 2007

(30) Foreign Application Priority Data
Oct. 6, 2003  (JP) .................................. 2003-346858

(51) Int. Cl.
*A01N 37/00* (2006.01)
(52) U.S. Cl.
USPC ........................................................ 514/557
(58) Field of Classification Search
USPC .................... 514/183, 557; 424/427
See application file for complete search history.

(56) References Cited

U.S. PATENT DOCUMENTS

| | | | |
|---|---|---|---|
| 5,116,868 A * | 5/1992 | Chen et al. .................... | 514/546 |
| 5,811,446 A * | 9/1998 | Thomas ........................ | 514/399 |
| 5,994,372 A * | 11/1999 | Yaksh ........................... | 514/327 |
| 6,495,598 B1 * | 12/2002 | Yoneda et al. ................ | 514/546 |

FOREIGN PATENT DOCUMENTS

| | | |
|---|---|---|
| EP | 1 125 575 A1 | 8/2001 |
| JP | 6-345653 A | 12/1994 |
| JP | 10-265378 A | 10/1998 |
| JP | 2000-281563 A | 10/2000 |
| JP | 2001-89366 A | 4/2001 |
| JP | 2002-543132 A | 12/2002 |
| JP | 2003-504397 A | 2/2003 |
| JP | 2003-313123 | * 11/2003 |
| JP | 2003-313124 A | 11/2003 |
| WO | WO-00/66122 A1 | 11/2000 |
| WO | WO-01/05388 A2 | 1/2001 |
| WO | WO-01/41806 A1 | 6/2001 |
| WO | WO-01/51065 A1 | 7/2001 |

OTHER PUBLICATIONS

Julie M. Albietz, et al, Chronic Dry Eye and Regression After Laser in situ Keratomileusis for Mypoia, 30 J. Cataract Refract. Surg. 675 (Mar. 2004).*
Hitoshi Watanabe, The Journal of the Eye, 1997, vol. 14, No. 11, pp. 1647 to 1653.
Ikuko Toda et al., The Journal of the Eye, 1991, vol. 8, No. 7, pp. 1021 to 1027.
Satoshi Suzuki et al., Nichigankaishi, 1997, vol. 101, No. 1, pp. 52 to 56.
Tsutomu Inatomi, Journal of Japan Contact Lens Society, 1999, vol. 41, No. 4, pp. S7-S13.
Murato Doru, The Japanese journal of opthalmic caring, May 1, 2003, vol. 5, No. 5, pp. 406 to 410.
Zhang, Y. L. et al., Journal of Colloid and Interface Science, Jun. 1, 2003, vol. 262, No. 1, pp. 130 to 148.
Tsutomu Inatomi, Journal of Japan Contact Lens Socitey, 1999, vol. 41, No. 4, pp. S7-S13.
Zhang, Y.L. et al., Journal of Colloid and Interface Science, Jun. 1, 2003, vol. 262, No. 1, pp. 130 to 148.
European Search Report dated Jul. 30, 2009.

* cited by examiner

*Primary Examiner* — Sean Basquill
(74) *Attorney, Agent, or Firm* — Birch, Stewart, Kolasch & Birch, LLP (57) ABSTRACT

There are provided an ophthalmic composition that comprises 3-hydroxybutyric acid and/or salts thereof as active ingredients and is used to prevent desiccation of eyes and an ophthalmic composition that is used to treat tear dysfunction. By use of the ophthalmic compositions of the present invention, desiccation of the eyes can be inhibited and tear dysfunction can be treated. Therefore, by use of the compositions, discomforts caused by tear dysfunction, such as desiccation of the eyes, foreign-body sensation, feeling of discomfort on the eyes and eye strain, can be improved. Further, the ophthalmic compositions of the present invention can inhibit diseases caused by tear dysfunction, exemplified by development of dry eye and suspected dry eye which are dysfunctions related to desiccation of the eyes, particularly, development of diseases caused by tear dysfunction without injuries on the keratoconjunctive.

19 Claims, 4 Drawing Sheets

OPHTHALMIC COMPOSITION FOR TREATING TEAR DYSFUNCTION

TECHNICAL FIELD

The present invention relates to an ophthalmic composition having an effect of preventing desiccation of eyes and to an ophthalmic composition for treating tear dysfunction. More specifically, it relates to an ophthalmic composition which comprises 3-hydroxybutyric acid and/or salts thereof as active ingredients and is used to prevent desiccation of eyes, and to an ophthalmic composition which is used to treat tear dysfunction.

BACKGROUND ART

Tear is a thin liquid layer having a thickness of about 7 μm and covering the outermost layer of a ocular surface. The tear has a three-layer structure comprising, from the surface, a lipid layer, an aqueous layer and a mucin layer, and these layers influence one another to form the structure of the tear film. Further, each of the layers of the tear contains various components such as proteins, e.g., lactoferrin, lysozyme, IgA, IgG and albumin, wax, cholesterol, glucide, and mucin. Illustrative examples of the functions of the tear containing these components include keeping the ocular surface wet, preventing the eyes from infection with pathogens coming from the outside, supplying a number of physiologically active substances, and supplying oxygen to the cornea that is an avascular organ.

As described above, tear has a variety of functions. However, for example, when the amount of secretion of the tear is decreased due to the occurrence of dysfunction in secretion of the tear or when the amount of evaporation of the tear is increased due to the occurrence of dysfunction in the quality of the tear, the functions of the tear may not be exercised normally. When such tear dysfunctions occur, desiccation of the eyes is found as a subjective symptom. In recent years, along with an increased level of desiccation in a room due to wide use of air conditioners and increase of VDT operations on personal computers and the like, the number of patients who complain about discomforts caused by tear dysfunctions, such as desiccation of the eyes, foreign-body sensation, feeling of discomfort on the eyes and eye strain has been increasing. Further, a symptom in which an injury has occurred on the keratoconjunctive epithelium along with such tear dysfunctions is defined as dry eye. However, in the broad sense, even a case where dysfunctions in the secretion and quality of tear are seen and no injury is seen on the keratoconjunctive epithelium is also considered as suspected dry eye. Thus, it is conceived that by using an ophthalmic composition having an effect of treating tear dysfunctions, e.g., increasing the amount of secretion of tear or reducing the amount of evaporation of tear by improving the quality of the tear, discomforts caused by tear dysfunctions, such as desiccation of the eyes, foreign-body sensation, feeling of discomfort on the eyes and eye strain can be improved, and development of diseases caused by tear dysfunctions, such as dry eye and suspected dry eye which are dysfunctions related to desiccation of the eyes can be inhibited. Illustrative examples of the dry eye and suspected dry eye include diseases such as hypolacrimation, alacrima, xerophthalmia, Sjogren's syndrome, Stevens-Johnson syndrome, ocular pemphigus, marginal blepharitis, dysfunctions of lidaperture and sensory nerves, dry eye associated with allergic conjunctivitis, viral conjunctivitis and cataract operation, BUT-shortened dry eye characterized in that only a tear film breakup time (hereinafter abbreviated as "BUT") which is one of the test method for diagnosis of tear is shortened, and symptoms caused by VDT operations which have been increasing in recent years.

At present, as a method of alleviating discomforts such as desiccation of the eyes and a method of alleviating or treating dry eye and suspected dry eye, a method comprising applying artificial tear from the outside to cover a deficiency of tear and a method comprising closing punctum are known, for example. Further, to treat injuries on the keratoconjunctive epithelium which have occurred due to dysfunctions in the secretion and quality of tear, a method using eye-drops containing sodium hyaluronate is also known, for example. However, the effects of all the above methods are temporary. Further, these methods are intended to treat injuries on the keratoconjunctive which are caused by tear dysfunctions and cannot inhibit the occurrence of dry eye and suspected dry eye and are merely symptomatic treatments. For these reasons, these methods are unsatisfactory. Therefore, not such symptomatic treatments as described above, but, for example, an ophthalmic composition having an effect of preventing desiccation of eyes and an ophthalmic composition for treating tear dysfunctions have been needed so as to improve discomforts caused by tear dysfunctions, such as desiccation of the eyes, foreign-body sensation, feeling of discomfort on the eyes and eye strain and to inhibit the occurrence of dry eye and suspected dry eye.

Heretofore, to prevent desiccation of the surface of the keratoconjunctive, an eye drop which contains glucomannan as an active ingredient (for example, refer to Patent Publication 1) and an eye solution which contains trimethylglycine (for example, refer to Patent Publication 2) have been disclosed. Further, it is also disclosed that a composition containing a $\beta_2$ adrenaline receptor agonist as an active ingredient can be used as an agent for treating or preventing diseases related to dry eye or the keratoconjunctive sicca (for example, refer to Patent Publication 3).

Further, as preparations for treating dry eye, in the test method for diagnosis of tear such as BUT, a dry eye treating agent which contains a macrolide compound having an excellent improving effect as an active ingredient (for example, refer to Patent Publication 4) and a composition for treating tear secretion dysfunctions including dry eye which contains a fatty acid derivative as an active ingredient (for example, refer to Patent Publication 5) are disclosed.

Meanwhile, with respect to 3-hydroxybutyric acid which is used as an active ingredient in the present invention, the present applicant has proposed a therapeutic agent for ectocornea injury (for example, refer to Patent Publication 6) and a cornea turbidity inhibitor (for example, refer to Patent Publication 7) as ophthalmic therapeutic preparations containing 3-hydroxybutyric acid as an active ingredient. However, with respect to an ophthalmic composition containing 3-hydroxybutyric acid, no reports have been made on use thereof for preventing desiccation of eyes and for treating tear dysfunction.

Patent Publication 1 JP-A 6-345653 (the term "JP-A" as used herein means an "unexamined published Japanese patent application")
Patent Publication 2 JP-A 2000-281563
Patent Publication 3 WO01/041806
Patent Publication 4 JP-A 2002-543132
Patent Publication 5 JP-A 2003-504397
Patent Publication 6 JP-A 10-265378
Patent Publication 7 JP-A 2001-89366

DISCLOSURE OF THE INVENTION

An object of the present invention is to provide an ophthalmic composition having an effect of preventing desiccation of eyes and an ophthalmic composition for treating tear dysfunction.

Other objects and advantages of the present invention will become apparent from the following description.

According to the present invention, the above object and advantage of the present invention are achieved by an ophthalmic composition which comprises 3-hydroxybutyric acid and/or salts thereof as active ingredients and is used to prevent desiccation of eyes, and an ophthalmic composition which is used to treat tear dysfunction.

BEST MODE FOR CARRYING OUT THE INVENTION

The ophthalmic composition of the present invention contains 3-hydroxybutyric acid and/or salts thereof as active ingredients. 3-hydroxybutyric acid is known to have a D form, a D,L-racemic form and an L form with respect to the configuration of the C3 position of its chemical structural formula. 3-hydroxybutyric acid having any of the structures can be used in the present invention. Further, as the salt of 3-hydroxybutyric acid, at least one compound selected from the group consisting of a sodium salt, a potassium salt, an L-lysine salt, an L-hystidine salt and an L-arginine salt is preferably selected as appropriate. These 3-hydroxybutyric acid and/or salts thereof can be used alone or in combination of two or more as appropriate. The concentration of 3-hydroxybutyric acid and/or salts thereof in the ophthalmic composition of the present invention is determined suitably according to the age and severity of the symptom of a patient or purpose of its use and, preferably ranges from 0.8 to 800 mmol/L, more preferably from 4 to 400 mmol/L, much more preferably from 8 to 240 mmol/L, particularly preferably from 10 to 150 mmol/L.

The ophthalmic composition of the present invention is used for preventing desiccation of eyes. In the present invention, preventing desiccation of eyes indicates treatment of tear dysfunction. Further, in the present invention, the tear dysfunction refers to when the amount of secretion of tear is decreased due to the occurrence of dysfunction in the secretion of tear or when the amount of evaporation of tear is increased due to the occurrence of dysfunction in the quality of tear, especially, to the above cases of tear dysfunctions without injuries on the keratoconjunctive. Along with these dysfunctions, problems may occur in the stability of tear and the retention of tear on the surface of the eye. For example, such phenomena as appearance of dry spots, shortening of BUT and dysfunctions in the microvilli/microvillus of the keratoconjunctive epithelium cells are observed. These phenomena cause discomforts caused by tear dysfunctions, such as desiccation of the eyes, foreign-body sensation, feeling of discomfort on the eyes and eye strain, thereby causing dry eye and suspected dry eye which are injuries associated with desiccation of the eyes. Therefore, preventing desiccation of eyes and treatment of tear dysfunction in the present invention refer to treatment of the above tear dysfunctions, improvements of discomforts caused by tear dysfunctions such as desiccation of the eyes, foreign-body sensation, feeling of discomfort on the eyes and eye strain, and inhibition of the occurrences of diseases caused by tear dysfunctions, especially, inhibition of the occurrences of diseases caused by tear dysfunction without injuries on the keratoconjunctives. Further, in the present invention, such a treatment of tear dysfunction includes those achieved by an improvement in the stability of tear film and/or an improvement in the retention of tears on the keratoconjunctive. Illustrative examples of the dry eye and suspected dry eye include diseases such as hypolacrimation, alacrima, xerophthalmia, Sjogren's syndrome, Stevens-Johnson syndrome, ocular pemphigus, marginal blepharitis, dysfunctions of lidaperture and sensory nerves, dry eye associated with allergic conjunctivitis, viral conjunctivitis and cataract operation, BUT-shortened dry eye characterized in that only BUT which is one of the test method for diagnosis of tear is shortened, and symptoms caused by VDT operations which have been increasing in recent years. Hereinafter, the improvement in the stability of the tear film and the improvement in the retention of tears on the keratoconjunctive will be described.

In the present invention, the improvement in the stability of the tear film indicates an improvement in the stability of at least one of a lipid layer, an aqueous layer and a mucin layer which constitute tear. Further, the improvement in the stability of the tear film in the present invention is achieved by an increase in the amount of secretion of at least one of the lipid layer, the aqueous layer and the mucin layer, for example. For example, it is achieved by an increase in the amount of secretion of at least one of components contained in tear such as proteins, e.g., lactoferrin, lysozyme, IgA, IgG and albumin, wax, cholesterol, glucide, and mucin. However, it may be achieved by other factors.

The layers which constitute tear affect one another and have an important function for the stability of tear. For example, the lipid layer serves to inhibit evaporation of tears by covering the whole aqueous layer and to prevent an outflow of tear from flowing out from the eyelid margin. The aqueous layer has the most of the thickness of tear and serves to retain the lubricity of the surface of the eye. The mucin layer covers the hydrophobic surface of the keratoconjunctive epithelium, thereby rendering the keratoconjunctive epithelium hydrophilic to prevent an outflow of tear from the surface of the eye. By use of the ophthalmic composition of the present invention, for example, the amount of secretion of at least one of the lipid layer, the aqueous layer and the mucin layer is increased, and among functions of the tear film mentioned above, for example, the effect of inhibiting evaporation of tears and the effect of preventing an outflow of tear from the surface of the eye can be attained. Specific examples of such effects include an effect of inhibiting appearance of dry spots and an effect of extending BUT. Thus, by use of the ophthalmic composition of the present invention, the stability of the tear film can be improved, so that preventing desiccation of eyes, i.e., treatment of tear dysfunction, can be achieved.

Meanwhile, in the present invention, the improvement in the retention of tear on the keratoconjunctive indicates an improvement in the retention of tear on the keratoconjunctive by maintaining keratoconjunctive epithelium cells in a normal state and/or restoring the keratoconjunctive epithelium cells to the normal state by use of the ophthalmic composition of the present invention. More specifically, by use of the ophthalmic composition of the present invention, the microvilli/microvillus of the keratoconjunctive epithelium cells can be maintained in a normal state and/or restored to the normal state. A large number of protruding microvilli/microvillus exist on the surfaces of the keratoconjunctive epithelium cells and serve to improve adhesion of the mucin layer of the tear layer and retain tear on the keratoconjunctive. However, it is known that keratoconjunctive epithelium cells which have diminished cell activity or are about to fall off show a diminished effect of retaining tear due to shortened microvilli/microvillus. Further, it is known that the protruding structures of the microvilli/microvillus become indistinct due to desiccation of the keratoconjunctive and the influences of preservative and the like. The ophthalmic composition of the present invention can maintain such microvilli/microvillus in a normal state and/or restore them to the normal state, thereby making it possible to improve the retention of tear on the keratoconjunctive. Thus, by use of the ophthalmic composition of the present invention, the retention of tear on the keratoconjunctive can be improved, so that preventing desiccation of eyes, i.e., treatment of tear dysfunction, can be achieved.

Since the ophthalmic composition of the present invention has the effect of improving the stability of the tear film and/or the effect of improving the retention of tear on the keratoconjunctive as described above, tear dysfunctions such as dysfunction in the secretion of tear and dysfunction in the quality of tear, particularly, tear dysfunctions without injuries on the keratoconjunctive, can be treated by use of the composition. Thus, discomforts caused by tear dysfunctions, such as desiccation of the eyes, foreign-body sensation, feeling of discomfort on the eyes and eye strain can be improved by use of the composition. Further, the occurrences of diseases caused by tear dysfunctions, such as dry eye and suspected dry eye that are injuries associated with desiccation of the eyes, particularly, the occurrences of diseases caused by tear dysfunctions without injuries on the keratoconjunctives, can be inhibited. Illustrative examples of the dry eye and suspected dry eye include diseases such as hypolacrimation, alacrima, xerophthalmia, Sjogren's syndrome, Stevens-Johnson syndrome, ocular pemphigus, marginal blepharitis, dysfunctions of lidaperture and sensory nerves, dry eye associated with allergic conjunctivitis, viral conjunctivitis and cataract operation, BUT-shortened dry eye characterized in that only BUT which is one of the test method for diagnosis of tear is shortened, and symptoms caused by VDT operations which have been increasing in recent years.

Further, the ophthalmic composition of the present invention is preferably used on patients having discomforts such as desiccation of the eyes, foreign-body sensation, feeling of discomfort on the eyes and eye strain. Further, the ophthalmic composition of the present invention is preferably used on patients having tear dysfunctions such as dysfunction in the secretion of tear and dysfunction in the quality of tear and preferably used for treating the tear dysfunctions of patients without injuries on the keratoconjunctive. In addition, the ophthalmic composition of the present invention is preferably used for inhibiting the occurrences of diseases caused by tear dysfunctions and more preferably used for inhibiting the occurrences of diseases caused by tear dysfunctions without injuries on the keratoconjunctive.

In the present invention, the ophthalmic composition refers to a medicinal composition used for preventing desiccation of eyes. Accordingly, its dosage form is preferably a dosage form selected from an eye drop, an eye wash and an eye ointment that are parenteral formulations and is particularly preferably an eye drop. In addition, the ophthalmic composition may also be a formulation which is not directly administered to the eyes such as an oral formulation as long as it is administered for the purpose of treating or preventing the disease of the eyes.

The ophthalmic composition of the present invention contains 3-hydroxybutyric acid as an active ingredient and may also contain various other components as required as long as preventing desiccation of eyes and treatment of tear dysfunctions by 3-hydroxybutyric acid are not hindered. For example, when the ophthalmic composition of the present invention is to be used as an eye drop, the composition can contain various additives such as a buffer, an isotonic agent, a stabilizer, a viscosity inducing agent and a pH regulating agent and other components as required to attain the stability and ease of administration of the eye drop. These various components can be contained alone or in combination of two or more as appropriate. In most cases, the components are preferably contained in combination of two or more. Hereinafter, a description will be given to a case where the ophthalmic composition of the present invention is used as an eye drop. However, the present invention shall not be limited thereto.

The buffer mentioned above can be contained for the purpose of stabilizing the pH of an eye drop when the ophthalmic composition of the present invention is used as the eye drop. The buffer may be anything that is generally used as buffer in eye drop. Illustrative examples thereof include boric acid, citric acid, phosphoric acid, tartaric acid, gluconic acid, acetic acid, carbonic acid, and salts thereof. These may be used alone or in combination of two or more. The concentration of the buffer ranges preferably from 0.001 to 5 w/v %, more preferably from 0.01 to 1 w/v %.

The isotonic agent mentioned above can be contained for the purpose of adjusting the osmotic pressure of eye drop when the ophthalmic composition of the present invention is used as the eye drop. The isotonic agent may be anything that is generally used as isotonic agent in eye drop. Illustrative examples thereof include inorganic salts such as alkali or alkaline earth metal salts, e.g., sodium chloride, potassium chloride, calcium chloride, magnesium chloride and magnesium sulfate, and carbohydrates such as glucose, mannitol, sorbitol, xylitol, dextran and glycerin. These may be used alone or in combination of two or more. The concentration of the isotonic agent ranges preferably 0.001 from to 5 w/v %, more preferably from 0.01 to 3 w/v %.

The stabilizer mentioned above can be contained for the purpose of stabilizing the active ingredients of eye drop when the ophthalmic composition of the present invention is used as the eye drop. The stabilizer may be anything that is generally used as stabilizer in eye drop. Illustrative examples thereof include edetic acid and salts thereof, cyclodextrin, sulfite salts, citric acid and salts thereof, and dibutyl hydroxytoluene. These may be used alone or in combination of two or more. The concentration of the stabilizer ranges preferably from 0.001 to 5 w/v %, more preferably from 0.01 to 1 w/v %.

The viscosity inducing agent mentioned above can be contained for the purpose of adjusting the viscosity of eye drop when the ophthalmic composition of the present invention is used as the eye drop. The viscosity inducing agent may be anything that is generally used as viscosity inducing agent in eye drop. Illustrative examples thereof include polyols such as glycerine, ethylene glycol, propylene glycol, polyethylene glycol and polyvinyl alcohol, carbohydrates such as trehalose, sucrose, carboxymethylcellulose, hydroxyethylcellulose, hydroxypropylmethylcellulose and cyclodextrin, and carboxy vinyl polymers. In addition, polysaccharides such as xanthan gum, locust bean gum, gellan gum and carrageenan gum, hyaluronic acid and salts thereof, povidone, and castor oil can also be contained. These may be used alone or in combination of two or more. The concentration of the viscosity inducing agent ranges preferably from 0.001 to 10 w/v %, more preferably from 0.01 to 5 w/v %.

The pH regulating agent mentioned above can be contained for the purpose of adjusting the pH of eye drop when the ophthalmic composition of the present invention is used as the eye drop. The pH regulating agent may be anything that is generally used as pH regulating agent in eye drop. Illustrative examples thereof include sodium hydroxide, potassium hydroxide, sodium carbonate, sodium hydrogen carbonate, hydrochloric acid, citric acid, boric acid, phosphoric acid, acetic acid, tartaric acid, and salts thereof. These may be used alone or in combination of two or more. The pH of the ophthalmic composition of the present invention is adjusted to a desired pH by addition of an appropriate amount of the pH regulating agent.

The other components mentioned above can be contained in the ophthalmic composition of the present invention as the eye drop for the purpose of imparting effects corresponding to the components. The other components may be anything that is generally used as ophthalmic agents. Illustrative examples thereof include a decongestant, anti-inflammatory agent, astringent, antihistamine, local anesthetic, vitamins, amino acids, sulfa drug, refreshing agent and miotic agent. These may be used alone or in combination of two or more. When the ophthalmic composition of the present invention contains these components, it is preferably checked whether the components and their concentrations are not those which do not adversely affect preventing desiccation of eyes and treatment of tear dysfunctions by 3-hydroxybutyric acid which is an active ingredient in the present invention, according to the ages, symptoms and the like of patients.

Meanwhile, preservatives may also be contained in the eye drops for the purpose of imparting a preservative effect when the ophthalmic composition of the present invention is used as the eye drop. The preservative may be anything that is generally used as preservative in eye drop. Illustrative examples thereof include cationic preservatives such as parabens, e.g., methyl paraben, ethyl paraben, propyl paraben and butyl paraben, chlorhexidine gluconate, chlorobutanol, phenylethyl alcohol, benzyl alcohol, sodium dehydroacetate, sorbic acid and salts thereof, a quaternary ammonium cationic surfactant and chlorhexidine hydrochloride. Illustrative examples of the quaternary ammonium cationic surfactant include benzalkonium chloride, benzethonium chloride, and cetylpyridinium chloride. These may be used alone or in combination of two or more. The concentration of the preservative ranges preferably from 0.0001 to 0.1 w/v %, more preferably from 0.001 to 0.05 w/v %.

However, it is known that the preservative generally instabilizes the tear film and has an adverse effect on the keratoconjunctive epithelium cells. Further, since a tear exchange rate may be abnormal when there are/is dysfunction in the secretion of tear and/or dysfunction in the quality of tear, the preservative may remain in the conjunctival sac for a long time. Further, when the keratoconjunctive epithelium has injuries, the injuries may further deteriorate. Thus, since application of an eye drop containing the preservative may have a further adverse effect on tear and the keratoconjunctive epithelium, it is more preferred that the preservative be not contained. When not containing the preservative, the eye drop of the present invention is preferably filled in a container of the type that is disposed once used, i.e., "disposable container".

Further, when the ophthalmic composition of the present invention is used as an eye drop, it is preferred to adjust the pH after various constituents are combined. The range of the pH is not particularly limited as long as it is an acceptable range as an eye drop. For example, a pH of 4 to 10 is preferred, and a pH of 6 to 8.5 is more preferred. An eye drop having an acidic pH of less than 4 or an alkaline pH of more than 10 is not preferred because it may cause eye irritation or eye injuries.

Further, when the ophthalmic composition of the present invention is used as an eye drop, the osmotic pressure of the composition is not particularly limited as long as it is within a range acceptable as an eye drop. For example, it ranges preferably from 100 to 600 mOsm., more preferably from 150 to 500 mOsm.

The ophthalmic composition of the present invention can be prepared in accordance with a generally known method. The composition can be generally prepared by dissolving various components mentioned above in purified water (or sterilized purified water as required) sequentially. For example, when the composition is used as an eye drop containing a viscosity inducing agent, it can be obtained by dissolving the viscosity inducing agent in sterilized purified water firstly, followed by dissolving the active ingredients and various components in the solution, adjusting the pH as required, and then filling the solution in a container made of polyethylene terephthalate or the like under sterile conditions.

The dosage of the ophthalmic composition of the present invention is not particularly limited as long as it is within an ophthalmologically acceptable range. For example, when the composition is used in the form of an eye drop as described above, one to three drops at a time are generally applied for one to twenty times, particularly preferably for one to ten times, in a day.

EXAMPLES

Hereinafter, the present invention will be described more specifically with reference to Examples and Comparative Examples. However, the present invention shall not be limited to these Examples and Comparative Examples in any way.

Example 1

Air was blown against rats in a low humidity environment as described below to prepare rat dry eye models. An effect of sodium D-3-hydroxybutyrate (hereinafter abbreviated as "HBA.Na") which is an active ingredient in the present invention, i.e., its effect of improving the stability of tear film, was examined by use of the prepared rat dry eye models. That is, observation of dry spot areas in the tear film of the rats and measurement of BUT of the tear film were made.

(1) Animals Used

As the animals to be examined, there were used female SD rats of 8 weeks old that had been conditioned in an animal room where they were kept under light for 12 hours and in the dark for 12 hours at a room temperature of 23±2° C. and a relative humidity of 60±10%. The rats were kept in the animal room for 4 days.

(2) Method for Preparing Rat Dry Eye Models

After the conditioning, the rats were carried into a low humidity environment kept at a room temperature of 20±2° C. and a relative humidity of 25±5% to blow air against the rat by a fan at a wind velocity of 2 to 4 m/s. Air was blown with the rat's front facing the blown air for 8 hours and with the rat allowed to move freely for 16 hours. This operation was conducted for 5 consecutive days. In the present example, the above environment is referred to as "dry environment".

(3) Evaluation of Rat Dry Eye Models

Prior to observation of the tear film and measurement of its BUT by HBA.Na instillation and PBS instillation, observation of dry spot areas in the tear film of the rat and measurement of BUT in the tear film in a normal environment (characterized by normal humidity and no air blowing) and the dry environment were carried out. As a result, it was found that rats in the dry environment showed significantly larger dry spot areas and significantly smaller BUT than rats in the normal environment (refer to FIGS. 1 and 2). Consequently, it was found that the tear layer of the rat becomes unstable in the dry environment. Accordingly, it was confirmed that the present models were dry eye models with dysfunction in tear.

(4) Preparation of Test Drugs and Instillation Method

As the compositions according to the present invention, eye drops prepared by dissolving HBA.Na in phosphate buffer sodium solutions (hereinafter abbreviated as "PBS") to 40, 80 and 120 mmol/L were prepared. Further, as a comparative solution, an eye drop comprising only PBS was used. HBA.Na of each concentration was applied to the right eye of a rat, and PBS was applied to the left eye of the rat. The eye drops were prepared to have a pH of 7.4 and an osmotic pressure of 280 mOsm. The first application of the eye drops was carried out immediately after the rats were placed in the dry environment such that the rats faced wind at the front, and the eye drops were then applied every two hours for a total of four times. On the second and subsequent days, the first application of the eye drops was also carried out immediately after the rats were placed such that they faced wind at the front, and the eye drops were then applied every two hours for a total of four times. This operation was conducted for 5 days.

(5) Observation of Tear Film and Evaluation Method

Figure 1:
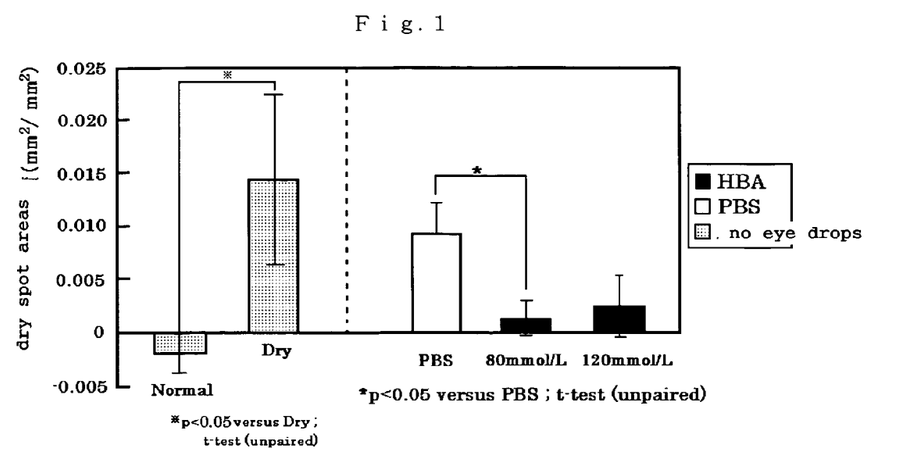
FIG. 1 shows dry spot areas per unit area of rats in a normal environment and a dry environment and dry spot areas per unit area when sodium D-3-hydroxybutyrate (hereinafter abbreviated as "HBA.Na") and phosphate buffer sodium solution (hereinafter abbreviated as "PBS") were applied to the eyes of rats in the dry environment.

After passage of two hours from the last application of the eye drops on the fifth day, a xylazine hydrochloride/ketamine hydrochloride mixed solution was injected (2 ml/kg) into the rats to anesthetize them. The rats were fixed, forced to blink and then allowed to open the eyes. Dry spot areas had been observed for 5 minutes since the eye-opening by use of a dry eye observation device "DR-1" (product of KOWA CO., LTD.), and the observed images were recorded on a videotape. The observed images were analyzed by use of image analysis software "Scion Image (version 4.02β)" (product of Scion Corporation) to determine a dry spot area per unit area [dry spot area (pixel)/area of observed area on the cornea (pixel)]. From the area, a dry spot area per unit area of the cornea [dry spot area (mm$^2$)/area of observed area on the cornea (mm$^2$)] was calculated by use of a conversion formula (1 pixel=0.0000195 mm$^2$) and evaluated. The dry spot area was calculated based on an increase and decrease from the eye-opening. The results are shown in FIG. 1. In the present example, the above procedure was conducted for HBA.Na concentrations of 80 and 120 mmol/L, and each of the HBA.Na concentrations was evaluated based on 12 eyes of 12 rats.

(6) Measurement of Tear Film Breakup Time (Hereinafter Abbreviated as "BUT") and Evaluation Method After passage of two hours from the last application of the eye drops on the fifth day, a xylazine hydrochloride/ketamine hydrochloride mixed solution was injected (2 ml/kg) into the rats to anesthetize them. After 1% fluorescein was added to the eyes of the rats and the rats were forced to blink a few times, BUT was measured. The above procedure was conducted for HBA.Na concentrations of 40, 80 and 120 mmol/L, and each of the HBA.Na concentrations was evaluated based on 8 eyes of 8 rats. The results were shown in FIG. 2.

It was found from the results shown in FIG. 1 that the tear film of the rat given the eye drop containing 80 mmol/l of HBA.Na which was an active ingredient in the present invention showed a significantly smaller dry spot area (p<0.05) than the tear film of the rat given PBS which was a comparative solution. Further, there was seen a tendency that when the eye drop containing 120 mmol/l of HBA.Na was given, the dry spot area also became smaller than that when PBS was given. This indicates that the tear film of the rat prepared in the dry environment is unstable, the tear film is not stabilized by application of PBS, tear disappears on the keratoconjunctive immediately after blinking, and dry spots appear. Meanwhile, it was confirmed that when the eye drop containing HBA.Na that was an active ingredient in the present invention was applied to the rat prepared under the same condition, the tear film showed a smaller dry spot area and improved stability. It was confirmed from these results that the ophthalmic composition of the present invention containing HBA.Na had an effect of improving the stability of the tear film.

Figure 2:
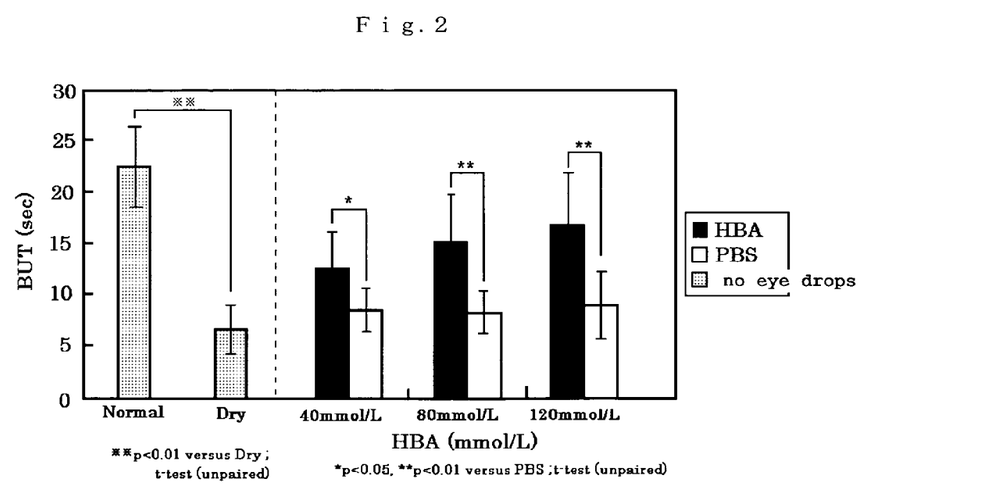
FIG. 2 shows BUTs of rats in the normal environment and the dry environment and also shows BUTs when HBA.Na and PBS were applied to the eyes of rats in the dry environment.

Further, it was found from the results shown in FIG. 2 that BUT extended more significantly by application of HBA.Na of any concentration than application of PBS. This indicates that even if PBS was applied to the rat prepared in the dry environment that had an unstable tear film and shortened BUT, the stability of the tear film is not improved. Meanwhile, it was confirmed that when the eye drop containing HBA.Na was applied to the rat prepared under the same condition, BUT was extended and the stability of the tear film was improved. It was confirmed from these results that the ophthalmic composition of the present invention containing HBA.Na had an effect of improving the stability of the tear film.

As described above, it was confirmed that the ophthalmic composition of the present invention had an effect of improving the stability of the tear film and was effective in preventing desiccation of eyes and treating tear dysfunction.

Example 2

By use of the rat dry eye models described in Example 1, the corneal epithelial cells of the rats after HBA.Na and PBS were applied were observed by a scanning electron microscope (hereinafter abbreviated as "SEM").

(i) Preparation of Samples

Samples were prepared in the following manner.

Figure 3:
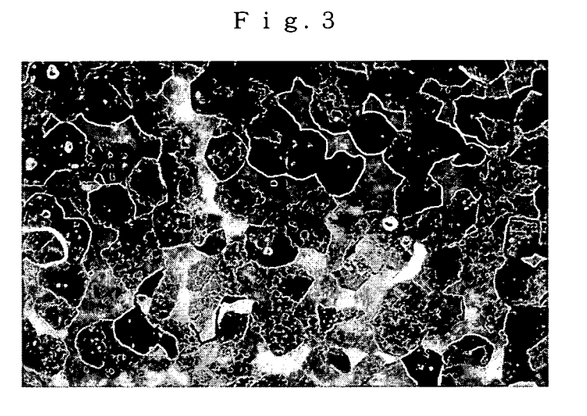
FIG. 3 shows a scanning electron microscopy observation photograph of the cornea of a rat in the normal environment.
Figure 4:
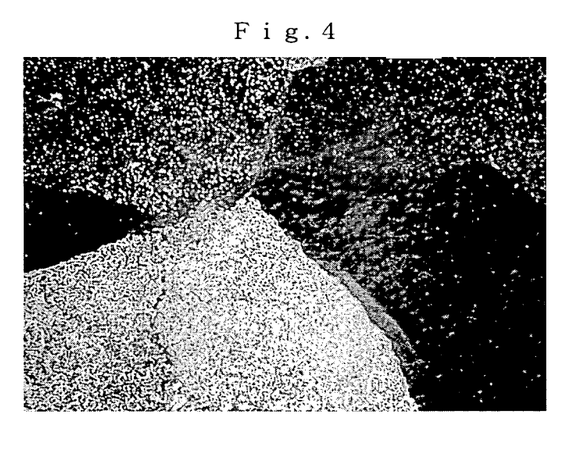
FIG. 4 shows a macrophotograph of FIG. 3.
Figure 5:
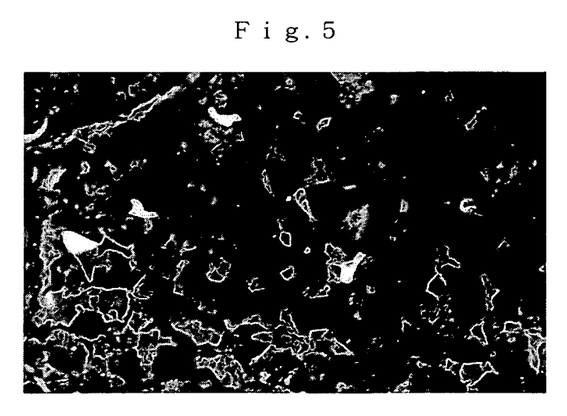
FIG. 5 shows a scanning electron microscopy observation photograph of the cornea of a rat in the dry environment.
Figure 6:
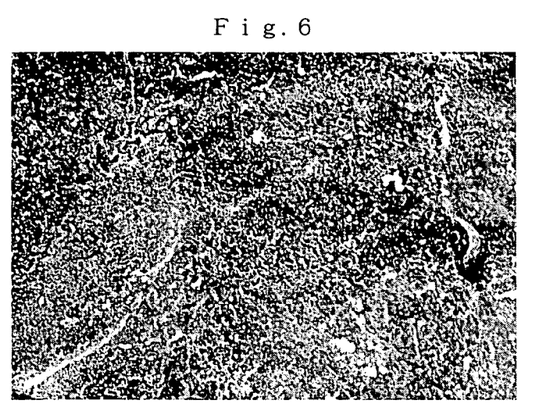
FIG. 6 shows a macrophotograph of FIG. 5.
Figure 7:
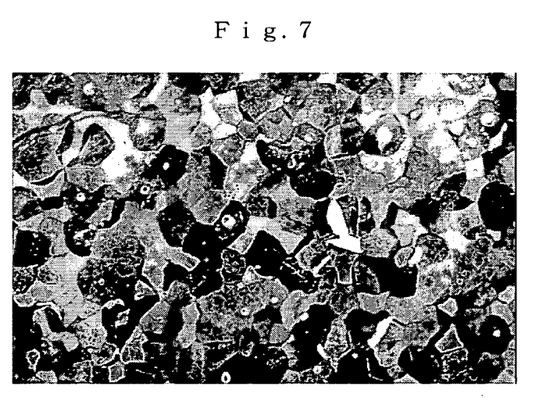
FIG. 7 shows a scanning electron microscopy observation photograph of the cornea of a rat in the dry environment when HBA.Na was applied to the eye of the rat.
Figure 8:
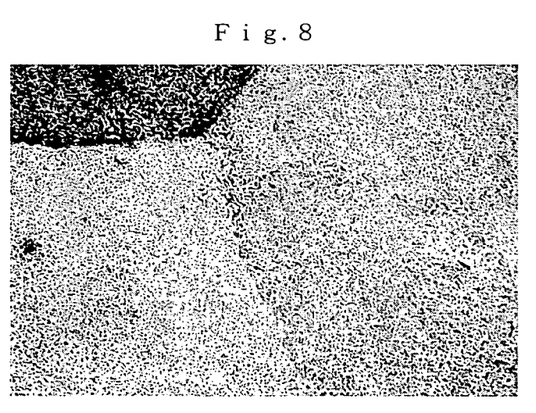
FIG. 8 shows a macrophotograph of FIG. 7.
Figure 9:
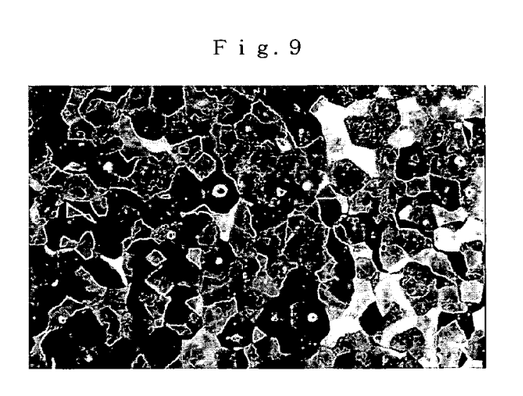
FIG. 9 shows a scanning electron microscopy observation photograph of the cornea of a rat in the dry environment when PBS was applied to the eye of the rat.
Figure 10:
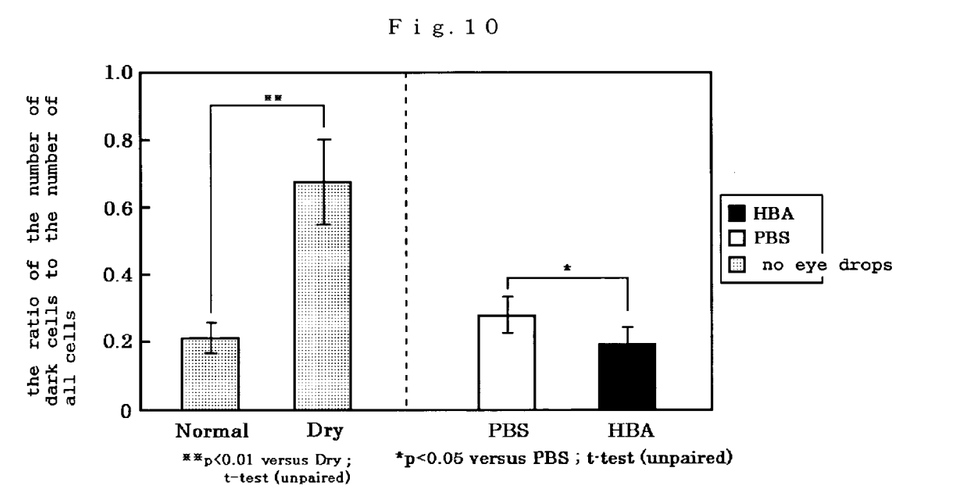
FIG. 10 shows the proportions of dark cells in the corneas of rats in the normal environment and the dry environment and also shows the proportions of dark cells in the corneas of rats in the dry environment when HBA.Na and PBS were applied to the eyes of the rats.

(1) In accordance with the methods described (1), (2) and (4) of Example 1, after 80 mmol/l of HBA.Na and a PBS solution were applied for 5 days, the corneas of the rats were removed immediately and washed with a phosphate buffer (hereinafter abbreviated as "PB"). After washed, the corneas were immersed in 2.5% glutaraldehyde-0.1 mol/l PB and pre-fixed at 4° C. for 20 minutes.
(2) The corneas were fully washed with 0.1 mol/l PB and post-fixed in 1% osmium tetraoxide—0.1 mol/l PB at 4° C. for 1 hour.
(3) The corneas were fully washed with 0.1 mol/l PB and dehydrated with ethanol ascending series.
(4) Ethanol was removed and replaced by t-butyl alcohol.
(5) The samples were freeze-dried and then bonded to sample stages.
(6) The samples were coated with platinum.
(ii) Observation by SEM Prior to observation by an SEM after applications of HBA.Na and PBS, the corneas of rats in the normal environment and dry environment were observed by an SEM (X-650 of Hitachi, Ltd.) and photographed for the purpose of confirmation. FIG. 3 shows the result of the normal environment, FIG. 4 shows a macrophotograph of FIG. 3, FIG. 5 shows the result of the dry environment, and FIG. 6 shows a macrophotograph of FIG. 5. Further, as the results of observing the samples prepared in the above (i) by the SEM, FIG. 7 shows the result of applying HBA.Na to the samples, FIG. 8 shows a macrophotograph of FIG. 7 and FIG. 9 shows the result of applying PBS to the samples.
(iii) Image Analysis The photographs taken by the above method were subjected to image analysis to calculate the proportion of the number of dark cells. In the analysis, 6 spots of a certain area were selected randomly from the photograph, the numbers of cells and dark cells within the areas were counted, and the ratio of the number of dark cells to the number of all cells was calculated. The results are shown in FIG. 10.

In observation of corneal epithelial cells by an SEM, it is known that according to the degree of brightness of cells, three kinds of polygonal cells, i.e., bright cells which show high cell activity and have long microvilli/microvillus, intermediate cells which have shortened microvilli/microvillus, and dark cells having microvilli/microvillus whose protruding structures are lost and about to fall off, are observed.

As already described, since it is known that keratoconjunctive epithelial cells (dark cells) having shortened microvilli/microvillus show a reduced tear retaining effect, a high proportion of dark cells indicates that adhesion of the mucin layer of tear is poor and retention of tear on the keratoconjunctive is low, while a low proportion of dark cells indicates that adhesion of the mucin layer of tear is good and retention of tear on the keratoconjunctive is high.

It is understood from FIGS. 3 and 5 that the rat in the dry environment has a higher proportion of dark cells than that in the normal environment. Further, as is clear from FIGS. 4 and 6, it was confirmed that the protruding structures of the microvilli/microvillus of the corneal epithelial cells of the rat in the dry environment were lost. It is understood from these results that the microvilli/microvillus of the corneal epithelial cells of rats are lost in the dry environment. This indicates that retention of tear on the cornea deteriorates. Consequently, it was confirmed that the present model is a dry eye model with tear dysfunction.

Further, it is understood from FIGS. 7 and 9 that the corneal epithelial cells of the rat given 80 mmol/l of HBA.Na show a significantly lower proportion of dark cells than the corneal epithelial cells of the rat given PBS (refer to FIG. 10) and show a similar condition to that of the corneal epithelial cells of the rat in the normal environment shown in FIG. 3. Further, it was confirmed from comparison of FIG. 6 with FIG. 8 that when HBA.Na was applied to the corneal epithelial cells of the rat in the dry environment, the microvilli/microvillus of the corneal epithelial cells of the rat were retained in a normal state and/or restored to the normal state. In addition, it was found that the condition thereof was similar to the condition of the corneal epithelial cells of the rat in the normal environment shown in FIG. 4.

It was confirmed from these results that the ophthalmic composition of the present invention containing HBA.Na had an effect of retaining the microvilli/microvillus of corneal epithelial cells in a normal state and/or restoring them to the normal state. Therefore, it was confirmed that the ophthalmic composition of the present invention had an effect of improving the retention of tear and was effective in preventing desiccation of eyes and treating tear dysfunction.

As is obvious from the above description, the ophthalmic composition of the present invention can prevent desiccation of eyes and treat tear dysfunction by containing 3-hydroxybutyric acid and/or salts thereof as active ingredients. Accordingly, by use of the composition, discomforts caused by tear dysfunction, such as desiccation of the eyes, foreign-body sensation, feeling of discomfort on the eyes and eye strain, can be improved. Further, the ophthalmic composition of the present invention can inhibit development of diseases caused by tear dysfunction, e.g., dry eye and suspected dry eye which are dysfunction associated with desiccation of the eyes, particularly, development of diseases caused by tear dysfunction without injuries on the keratoconjunctive.

The invention claimed is:

1. A method for treating tear abnormality in a patient suffering from a tear abnormality, which comprises:
    administering to a patient having at least one tear abnormality selected from the group consisting of hypolacrimation, alacrima, xerophthalmia, Sjogren's syndrome, Stevens-Johnson syndrome, ocular pemphigus, marginal blepharitis, dysfunctions of lidaperture and sensory nerves, dry eye associated with allergic conjunctivitis and viral conjunctivitis, an ophthalmological eye drop composition comprising 3-hydroxybutyric acid and/or salts thereof as an active ingredient in an amount effective in treating the tear abnormality.

2. The method of treating tear abnormality of claim 1, wherein the treatment of the tear abnormality is achieved by an improvement in the stability of a tear layer and/or an improvement in the retention of tear on the keratoconjunctiva.

3. The method of treating tear abnormality of claim 2, wherein the improvement in the stability of the tear layer is achieved by inhibition of evaporation of tear.

4. The method of treating tear abnormality of claim 2, wherein the improvement in the stability of the tear layer is achieved by an improvement in tear layer breakup time.

5. The method of treating tear abnormality of claim 2, wherein the improvement in the retention of tear is achieved by retention of keratoconjunctiva epithelium cells in a normal state and/or restoration of the keratoconjunctiva epithelium cells to the normal state.

6. The method of treating tear abnormality of claim 2, wherein the improvement in the retention of tear is achieved by retention of the microvilli/microfolds of keratoconjunctiva epithelium cells in a normal state and/or restoration of the microvilli/microfolds of the keratoconjunctiva epithelium cells to the normal state.

7. The method of treating tear abnormality of claim 1, wherein the tear abnormality is tear abnormality without impairments on the keratoconjunctiva.

8. The method of treating tear abnormality of claim 1, wherein the treatment of the tear abnormality is inhibition of the occurrences of diseases caused by the tear abnormality.

9. The method of treating tear abnormality of claim 8, wherein the treatment of the tear abnormality is inhibition of the occurrences of diseases caused by the tear abnormality without impairments on the keratoconjunctiva.

10. The method of treating tear abnormality of claim 1, wherein the concentration of 3-hydroxybutyric acid and/or salts thereof is 0.8 to 800 mmol/l.

11. The method of treating tear abnormality of claim 1, wherein the concentration of 3-hydroxybutyric acid and/or salts thereof is 10 to 150 mmol/l.

12. A method for treating tear abnormality of claim 1, wherein said opthalmological composition is administered as one to three eye drops, one to twenty times per day.

13. A method for treating tear abnormality of claim 12, wherein said eye drops are administered one to ten times per day.

14. A method for treating tear abnormality in a patient suffering from a tear abnormality, which method comprises:
administering to a patient having at least one tear abnormality selected from the group consisting of hypolacrimation, alacrima, xerophthalmia, Sjogren's syndrome, Stevens-Johnson syndrome, ocular pemphigus, marginal blepharitis, dysfunctions of lidaperture and sensory nerves, dry eye associated with allergic conjunctivitis and viral conjunctivitis, an opthalmological composition comprising (i.) 0.8 to 800 mmol/l 3-hydroxybutyric acid and/or salts thereof as an active ingredient, (ii.) a buffer in a concentration ranging from 0.001 to 5 w/v %, and (iii.) a viscosity inducing agent in a concentration ranging from 0.1 to 5 w/v % in an amount effective for treating the tear abnormality, wherein said opthalmological composition is administered as one to three eye drops, one to twenty time per day.

15. The method of claim 1, wherein the ophthalmological eye drop composition further comprises at least one additive selected from the group consisting of a buffer, an isotonic agent, a stabilizer, a viscosity inducing agent and a pH regulating agent.

16. The method of claim 15, wherein the ophthalmological eye drop composition comprises a buffer in a concentration of 0.001 to 5 wt/vol %.

17. The method of claim 15, wherein the ophthalmological eye drop composition comprises an isotonic agent in a concentration of 0.001 to 5 wt/vol %.

18. The method of claim 15, wherein the ophthalmological eye drop composition comprises a stabilizer in a concentration of 0.001 to 5 wt/vol %.

19. The method of claim 15, wherein the ophthalmological eye drop composition comprises a viscosity inducing agent in a concentration of 0.001 to 10 wt/vol %.

* * * * *